United States Patent
Hersperger

[11] Patent Number: 6,136,821
[45] Date of Patent: Oct. 24, 2000

[54] NAPHTHYRIDINE DERIVATIVES

[75] Inventor: René Hersperger, Münchenstein, Switzerland

[73] Assignee: Novartis AG, Basel, Switzerland

[21] Appl. No.: 09/297,245

[22] PCT Filed: Oct. 24, 1997

[86] PCT No.: PCT/EP97/05898

§ 371 Date: Apr. 27, 1999

§ 102(e) Date: Apr. 27, 1999

[87] PCT Pub. No.: WO98/18796

PCT Pub. Date: May 7, 1998

[30] Foreign Application Priority Data

Oct. 28, 1996 [GB] United Kingdom .................. 9622386

[51] Int. Cl.[7] ........................ A61K 31/435; C07D 471/04
[52] U.S. Cl. ........................................... 514/300; 546/122
[58] Field of Search .............................. 546/122; 514/303

[56] References Cited

U.S. PATENT DOCUMENTS

| | | | |
|---|---|---|---|
| 4,956,371 | 9/1990 | Shoupe et al. | 514/307 |
| 4,980,359 | 12/1990 | Hasspacher et al. | 514/307 |
| 5,466,697 | 11/1995 | Wilhelm | 514/300 |

FOREIGN PATENT DOCUMENTS

| | | |
|---|---|---|
| 0172058 | 2/1986 | European Pat. Off. . |
| 2625743 | 7/1989 | France . |
| WO 98/35967 | 8/1998 | WIPO . |

OTHER PUBLICATIONS

Couture et al, J. Chem. Soc. Perkin Trans. 1, p. 2643–2646, 1995.
Giam et al, J. Chem. Soc. Chem. Communications, No. 5, p. 265–266, 1984.
Patent Abstracts of Japan, vol. 007, No. 053—Mar. 3, 1983.
Patent Abstracts of Japan, vol. 004, No. 002—Jan. 9, 1980.
Chemical Abstracts, vol. 101, No. 3—Jul. 16, 1984.

*Primary Examiner*—Bernard Dentz
*Attorney, Agent, or Firm*—Carol A. Loeschorn

[57] ABSTRACT

Novel 8-aryl-1,7-naphthyridines, in free or salt form, are PDE IV inhibitors and are thus useful as pharmaceuticals, e.g. for asthma therapy. Preferred compounds include compounds of formulae (I and II) wherein the R groups are as defined. Pharmaceutical compositions comprising the compounds, processes for preparation of the compounds and novel intermediates for use in the processes are disclosed.

20 Claims, No Drawings

NAPHTHYRIDINE DERIVATIVES

This application is a 371 of PCT/EP97/05898 filed Oct. 24, 1997.

The present invention relates to novel 8-aryl-1,7-naphthyridines, processes for their production, their use as pharmaceuticals and pharmaceutical compositions comprising them.

The present invention provides 8-aryl-1,7-naphthyridines, in free or pharmaceutically acceptable salt form. By "aryl" is meant a mono or bicyclic aromatic or heteroaromatic moiety having up to 10 aromatic non-hydrogen atoms and being linked to the 1,7-naphthyridine either directly (e.g., phenyl, pyridyl, tetrazolyl, benzofurazanyl, or benzothiadiazolyl) or via a methylene bridge (e.g., benzyl or pyridylmethyl); preferably a monocyclic aromatic moiety having up to six aromatic carbon atoms, up to two of which may be replaced with nitrogen, for example phenyl, benzyl, 4-pyridyl, or 4-pyridylmethyl, optionally bearing a carboxy, carboxy ester or hydroxy group. The 8-aryl moiety may optionally be further substituted, especially with an electron withdrawing substituent, e.g., nitro, nitrilo, imino, halogen or a halogen-containing substituent (e.g. trifluoromethyl), or cyano, preferably in the meta-position. For example, the 8-aryl moiety may be cyanophenyl, nitrophenyl, tetrazolylphenyl (e.g. tetrazol-1-ylphenyl), or chlorophenyl. Optionally, the double ring of the naphthyridine portion of the molecule may also be further substituted or disubstituted, especially 6-substituted, with hydroxy, alkyl, alkenyl, alkynyl, alkoxy, aryl, aryloxy, amino, arylamino, diarylamino, alkamino, dialkamino, arylamido, or alkamido, wherein "alk" refers to an aliphatic moiety of up to eight carbon atoms, optionally bearing a carboxy, or carboxy ester or hydroxy group and/or optionally containing an ether linkage and/or ester linkage.

In particular, the invention provides novel 8-phenyl- and 8-benzyl-1,7-naphthyridines, wherein the 1,7-naphthyridine double ring is optionally 6-substituted, e.g., as exemplified below, and the phenyl ring is optionally substituted by an electron withdrawing substituent such as nitro; e.g., compounds of Formula I:

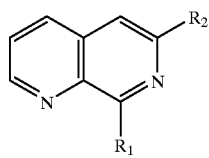

wherein
R$_1$ is phenyl, benzyl, 3-nitrophenyl, 3-chlorophenyl, 3-cyanophenyl, 3-(tetrazolyl)phenyl, benzofurazanyl, or benzothiadiazolyl;
R$_2$ is hydroxy, trifluoromethylsulfonyloxy, allyl, alkyl, alkenyl, alkynyl, alkoxy, aryl, aralkyl, aryloxy, amino, arylamino, diarylamino, alkamino, dialkamino, alkaryl, arylamido, or alkamido,
and esters and amides thereof;
in free or pharmaceutically acceptable salt form.

In formula I and elsewhere in the present description "alk" and "aryl" have the meanings as given above in relation to the 8-aryl-1,7-naphthyridines of the invention.

Preferably, R$_2$ is selected from hydroxy, amino, arylamino (e.g., phenylamino), aryl (e.g., phenyl), alkaryl (e.g. lower alkylphenyl), alkenyl (e.g., vinyl), alkynyl (e.g., ethynyl), alkoxy containing an ether linkage and/or ester linkage (e.g., methoxycarbonylmethoxy), and alkamido (e.g., acetamido).

In particular it has been surprisingly discovered that a wholly new class of 6,8-aryl-1,7-naphthyridines are useful as pharmaceuticals, in particular as orally active PDE 4 inhibitors, e.g. for the treatment of asthma.

Thus in a preferred embodiment the invention provides 6-(carboxyphenyl or carboxymethylphenyl)-8-(phenyl, benzo[c]thiadiazolyl or benzo[c]furazanyl)-1,7-naphthyridines, and esters and amides thereof, in free or pharmaceutically acceptable salt form.

More preferably, the invention provides 6-(4-carboxyphenyl or 4-carboxymethylphenyl)- 8-(phenyl, 4-benzo[c]thiadiazolyl or 4-benzo[c]furazanyl)-1,7-naphthyridines, and esters and amides thereof, in free or pharmaceutically acceptable salt form.

By benzo[c]thiadiazolyl and benzo[c]furazanyl are meant radicals of formula A and B respectively:

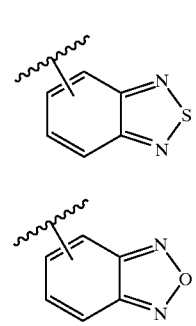

Thus in a particularly preferred embodiment the invention provides a compound of formula II

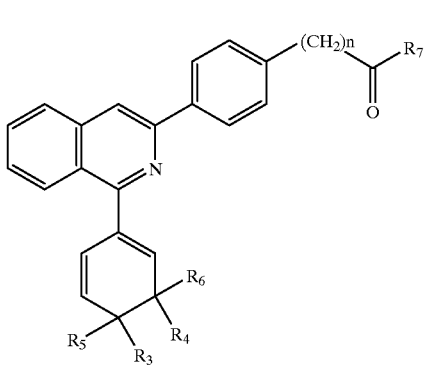

wherein
n is zero or one;
R$_7$ is hydroxy, amino, C$_{1-4}$alkylamino, or C$_{1-4}$alkoxy, preferably hydroxy or amino; and either
R$_3$ is H and R$_4$ is nitro, halo (e.g. chloro), cyano, or tetrazolyl (e.g. 1-tetrazolyl), and R$_5$ and R$_6$ together form an additional bond, or
R$_3$, R$_4$, R$_5$ and R$_6$ together are =N—O—N= or =N—S—N=;
and esters and amides thereof;
in free or pharmaceutically acceptable salt form.

Suitable pharmaceutically acceptable salt forms of the 8-aryl-1,7-naphthyridines, e.g., of Formula I or II, for pharmaceutical use are prepared by conventional means. For example, compounds having a free carboxylic acid group, e.g. compounds of formula II in which $R_7$ is OH, may be contacted with a suitable base, e.g. an amino sugar such as an N-methyl-glucamine, to provide a corresponding base addition salt. Conveniently such base addition salts may be water soluble.

The 8-aryl-1,7-naphthyridines of the invention, e.g., of formula I, may be prepared by reacting 2-cyano-3-pyridylacetonitrile a) with an acid, e.g., H—A, wherein A is a halogen, e.g., bromine, to obtain the compound of Formula III:

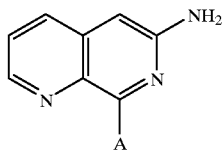

III which can then be further derivatized to obtain compounds of the invention, e.g., with a cross-coupling reaction using metal reagents in the presence of a palladium or nickel catalyst to form a carbon-carbon bond, for example a Stille, Suzuki, or Heck reaction, i.e., reacting a compound of formula III with a compound Y—$R_8$ wherein Y is a metallic leaving group, e.g., $B(OH)_2$—, $(CH_2)_3Sn$—$(CH_3(CH_2)_3)_3$Sn—, and $R_8$ is an 8-aryl moiety as defined above, e.g., benzyl or 3-nitrophenyl, to obtain the corresponding compound of formula IV

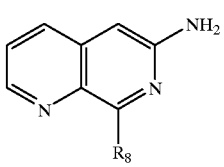

IV or b) with a Grignard reagent, e.g., $R_8$—MgBr, wherein $R_8$ is an 8-aryl moiety as defined above, e.g., benzyl or 3-nitrophenyl, to obtain the corresponding compound of formula IV; or c) with an alkali metal-alkanol, e.g. sodium-methanol, mixture to obtain a compound of formula III'

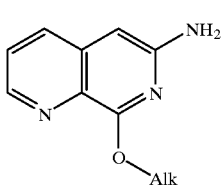

III' where Alk denotes a $C_1$–$C_8$ alkyl group, e.g. methyl. The —O—Alk substituent may be converted to halogen A, and the compound thereafter derivatised at the 8 position as described above for the compound of formula III.

The amino group in Formula III, III' or IV is amenable to further reaction, e.g., (i) activation with a suitable activating reagent, e.g., with trifluoromethane sulfonic acid and $NaNO_2$, to obtain the triflate of formula V:

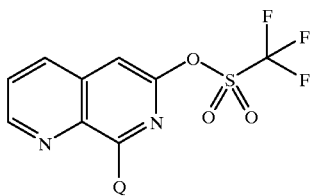

V wherein Q is either a halogen A as defined above, an —O—Alk substituent as defined above for the compound of formula III', or an 8-aryl moiety $R_8$ as defined above, which is a novel and highly useful intermediate for the preparation of compounds of the invention, e.g., when $R_2$ in Formula I is joined to the rest of the molecule via a carbon-carbon bond, the substitution can be accomplished, e.g., with a cross-coupling reaction using metal reagents in the presence of a palladium or nickel catalyst to form a carbon-carbon bond, for example a Stille, Suzuki, or Heck reaction, e.g., reacting a compound of Formula V wherein Q is $R_8$ with a compound of formula Y—$R_2$ wherein Y is a metallic leaving group as defined above and $R_2$ is the desired carbon substituent, e.g., alkyl, alkenyl, alkynyl, aryl or alkaryl as defined above for formula I, optionally in protected form, followed by deprotection if required; or (ii) alkyl or aryl substitution (e.g., by reaction with a corresponding alkyl halide or organometal) to give the desired secondary or tertiary amine; or (iii) acylation (e.g., by reaction with a carboxylic acid or an acid anhydride) to give the corresponding amide, using conventional procedures; or (iv) conversion to hydroxy, e.g., by reaction with $NaNO_2$ in the presence of a dilute acid, e.g., sulfuric acid, and optionally further derivatized, e.g., O-alkylated, for example by reaction with an alkyl halide under suitable reaction conditions.

The preferred 6-(carboxy-, or carboxymethyl- -phenyl)-8-(phenyl, benzo[c]thiadazolyl or benzo[c]furazanyl)-1,7-naphthyridines, or esters or amides thereof, e.g. of formula II, are conveniently prepared by the following method (A) for preparation of a 6-(carboxy- or carboxymethyl-phenyl)-8-(phenyl, benzo[c]thiadazolyl or benzo[c]furazanyl)-1,7-naphthyridines, or esters or amides thereof, reacting a 6-X-8-(phenyl, benzo[c]thiadazolyl or benzo[c]furazanyl)-1,7-naphthyridine with an X'-(carboxy-, or carboxymethyl- -phenyl) or ester or amide thereof, or reacting a 6-(carboxy- or carboxymethyl-phenyl)-8-X-1,7-naphthyridine or ester or amide thereof with an X'-(phenyl, benzo[c]thiadazolyl or benzo[c]furazanyl), wherein X and X' are leaving groups capable of participating in a cross-coupling reaction; for example, wherein X is trifluoromethylsulfonyloxy or halogen, e.g. bromine or chlorine, and X' is a metallic leaving group, e.g. substituted boron (e.g. —$B(OH)_2$, —$B(OAlk)_2$ or —$Balk_2$ where Alk is alkyl, e.g. methyl or ethyl) or trialkylstannyl (e.g. $(CH_3(CH_2)_3)_3Sn$— or $(CH_3)_3Sn$—) or a Grignard radical (e.g. MgBr; and/or (B) optionally reacting a 6-(carboxy- or carboxymethyl-phenyl)-8-(phenyl, benzo[c]thiadazolyl or benzo[c]furazanyl)-1,7-naphthyridine with a suitable amine, e.g. ammonia or $(C_{1-4})$alkylamine, to obtain the corresponding amide; and/or (C) optionally reacting a 6-(carboxy- or carboxymethyl-phenyl)-8-(phenyl, benzo[c]thiadazolyl or benzo[c]furazanyl)-1,7-naphthyridine with a suitable alcohol, e.g. a $(C_{1-4})$alcohol, to obtain the corresponding ester; and recovering the resulting 6-(carboxy- or carboxymethyl-phenyl)-8-(phenyl, benzo[c]thiadazolyl or benzo[c]furazanyl)-1,7-naphthyridine, or ester or amide thereof, in free or salt form.

Reaction conditions for step (A) are as known in the art for cross-coupling reactions using metal reagents, e.g. in the presence of a palladium or nickel catalyst, to form a carbon-carbon bond; for example, as in a Stille, Suzuki, or Heck reaction. Reaction conditions for steps (B) and (C) are as known in the art for preparation of amides from reaction of carboxylic acids and amines and for preparation of esters from carboxylic acids and alcohols, e.g. under acidic or basic conditions. Recovery and purification are by usual methods, e.g. by chromatography or crystallisation.

Thus in a preferred embodiment the invention provides a process for the preparation of a compound of formula II, as defined above, comprising reacting a compound of formula VI

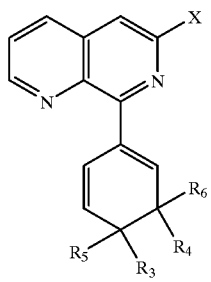

VI wherein $R_3$, $R_4$, $R_5$, $R_6$ and X are as defined above with a compound of formula VII

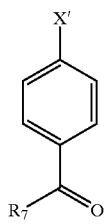

VII wherein $R_7$ and X' are as defined above, and recovering the compound of formula II thus obtained in free or salt form.

6-X-8-(phenyl, benzo[c]thiadazolyl or benzo[c]furazanyl)-1,7-naphthyridines and 6-(carboxy- or carboxymethyl- -phenyl)-8-X-1,7-naphthyridines or esters or amides thereof for use in the above reactions are suitably prepared by reacting 2-cyano-3-pyridylacetonitrile with an acid, e.g. H—A, where A is a halogen, e.g. bromine, to obtain a compound of formula III, and thereafter further derivatised as required, as described above.

The above described processes for the preparation of the 8-aryl-1,7-naphthyridines of the invention, in particular the preferred 6-(carboxy-, or carboxymethyl- -phenyl)-8-(phenyl, benzo[c]thiadazolyl or benzo[c]furazanyl)-1,7-naphthyridines and esters and amides thereof, are new as are the intermediates of formulae IV, V and VI, and these novel processes and intermediates are included within the scope of the present invention. It will be appreciated that compounds of formula V in which Q is $R_8$ and compounds of formula IV are encompassed by the 8-aryl-1,7-naphthyridines of the invention.

Thus in further aspects the invention provides intermediates of formula V'

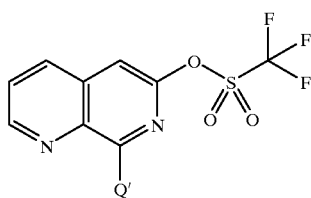

V' wherein Q' is halogen, or —O—Alk where Alk denotes a $C_1$–$C_8$ alkyl group, and formula VI

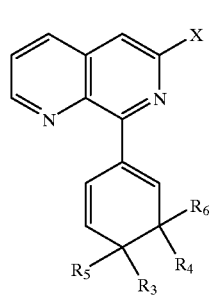

VI wherein $R_3$, $R_4$, $R_5$, $R_6$ and X are as defined above.

The following examples are illustrative of the invention.

EXAMPLES

Example 1

6-Amino-8-(3-nitrophenyl)-1,7-naphthyridine

A. 2-Cyano-3-pyridylacetonitrile

To a stirred suspension of 3-cyanomethylpyridine-N-oxide (30 g, 0.22 mol; for synthesis see Shigenobu Okuda, Michael M. Robison, J. Am. Chem. Soc. 81, 740 (1959)) in dichloromethane (200 ml) is added trimethylsilanecarbonitrile (26 g, 0.26 mol). To this suspension is added dimethylcarbamyl chloride (28 g, 0.26 mol). The mixture is stirred for 45 h. The solvent is removed and the residue dissolved in ethyl acetate. The solution is washed with 1 N NaOH and water and concentrated in vacuo. The product is purified by flash column chromatography on silica gel (15:2 toluene/acetone) affording the title compound. Mass M+H 144.1. Melting point 62–63° C.

B. 6-Amino-8-bromo-1,7-naphthyridine

Through a stirred solution of 2-Cyano-3-pyridylacetonitrile (3.6 g, 0.025 mol) in toluene (80 ml) is bubbled HBr for 5 h. Then, 4N NaOH is carefully added and the suspension stirred vigorously. The mixture is filtered and the product washed with water and dried. Crystallisation from toluene affords the title compound. Mass M+H 225. Melting point 188° C., decomposition.

C. 6-amino-8-(3-nitrophenyl)-1,7-naphthyridine

To a stirred solution of 6-amino-8-bromo-1,7-naphthyridine (4 g, 0.018 mol) in a mixture of tetrahydrofuran (80 ml) and aqueous $Na_2CO_3$ (34 ml, 2N) is added bis(dibenzylideneacetone)palladium (0.40 g, 0.0007 mol), triphenylphosphene (0.37 g, 0.0014 mol) and 3-nitrophenylboronic acid (3.7 g, 0.022 mol). The mixture is stirred for 16 h at 80° C. The mixture is filtered, ethyl acetate added and the mixture washed with 2N NaOH and water. The organic solvent is removed and the residue suspended in ether. Filtration affords the title compound. Mass M+H 267. mp 221–223° C.

Example 2

6-amino-8-(4-benzo[c]furazanyl)-1,7-naphthyridine

To a stirred solution of 6-amino-8-bromo-1,7-napthyridine (3.0 g, 13.4 mmol) in DMF (50 ml) are added bis(dibenzylidenacetone) palladium (308 mg, 0.54 mmol), triphenylphosphine (565 mg, 2.15 mmol) and 4-trimethylstannyl-benzo[c]furazanyl (4.92 g; 16.0 mmol). The mixture is kept at 125° for 4 h. Ethylacetate (500 ml) is added, followed by aqueous KF (40%, 100 ml). The mixture is stirred vigorously for 45 min and filtered. The organic phase is separated, washed with water and concentrated. The residue is taken up in ether (20 ml) stirred for 30 min (0°) and filtered to give the title compound (2.8 g). M+H=264 mp 244–250.

Example 3

6-Hydroxy-8-(3-nitrophenyl)-1,7-naphthyridine

To a solution of 6-amino-8-(3-nitrophenyl)-1,7-naphthyridine (500 mg, 1.87 mmol; prepared according to example 1) in concentrated sulfuric acid and water (3 ml, 2:1) is added sodium nitrate (155 mg, 2.25 mmol) at 4° C. After 30 minutes, the ice bath is removed, and the mixture is warmed to 70° C. for 30 minutes. the reaction mixture is poured onto ice, and the solution is neutralized by adding sodium bicarbonate. The precipitate is filtered and washed with water affording the title compound. mp 262–265° C.

Example 4

6-Methoxycarbonylmethoxy-8-(3-nitrophenyl)-1,7-naphthyridine

A suspension of 6-hydroxy-8-(3-nitrophenyl)-1,7-naphthyridine (107 mg, 0.40 mmol; produced according to the preceeding example, optionally without further purification), potassium carbonate (55 mg, 0.40 mmol) and bromoacetic acid methyl ester (37 μl, 0.4 mmol) is stirred for two hours in acetone-dimethylformamide (2 ml, 1:1) at ambient temperature. Ethyl acetate is added and the organic phase is washed with 2N NaOH. the solvent is removed in vacuo and the crude product is purified by preparative thin-layer chromatography to give the title compound. Mass M+H 340; mp 160–162° C.

Example 5

6-Acetamido-8-(3-nitrophenyl)-1,7-naphthyridine hydrochloride

A suspension of 6-amino-8-(3-nitrophenyl)-1,7-naphthyridine (300 mg, 1.1 mmol; prepared according to example 1) and acetic acid anhydride (0.12 ml, 1.2 mmol) in pyridine (1 ml) and dimethylformamide (3 ml) is kept at 80° C. for three hours. Water is added and the precipitate is filtered and throughly washed with water. Filtration affords the title product. Mass M+H 308; mp 235–238° C.

Example 6

6-Amino-8-benzyl-1,7-naphthyridine

To a solution of 2-cyano-3-pyridylacetonitrile (2 g, 0.014 mol) in toluene (20 ml) is added benzylmagnesium bromide 8.4 ml, 2N in tetrahydrofuran, 0.17 mol) at ambient temperature. After 1 h the reaction is quenched with a saturated solution of ammonium chloride. The product is extracted with ethyl acetate and the organic layer washed with 2N NaOH and water. The product is purified by flash column chromatography on silica gel (10:3 toluene/acetone) affording the title compound. Mass M+H 236; mp 113–116° C.

Example 7

6-Phenylamino-8-(3-nitrophenyl)-1,7-naphthyridine

To a solution of triphenylbismuth 182 mg, 0.41 mmol) in dichloromethane (0.5 ml) and tetrahydrofuran (0.5 ml) is added peracetic acid (0.083 ml, 40%). The mixture is stirred for 1 h. Then, a solution of 6-amino-8-(3-nitrophenyl)-1,7-naphthyridine (100 mg, 0.37 mmol; prepared according to example 1) in dichloromethane (0.5 ml) and THF (0.5 ml) is added. Copper (30 mg, 0.47 mmol) is added and the suspension is stirred for 40 h. The suspension is diluted with ethyl acetate and filtered. The filtrate is washed with 2N, $Na_2CO_3$ and water and the organic layer concentrated in vacuo. Preparative thin-layer chromatography (8:2 dichloromethane/n-hexane) affords the title compound. Mass M+H 343.1; mp 158–160° C.

Example 8

6-Trifluoromethylsulfonyloxy-8-(3-nitrophenyl-1,7-naphthyridine

To a solution of 6-amino-8-(3-nitrophenyl)-1,7-naphthyridine (1.24 g, 0.0047 mol; prepared according to example 1) in trifluoromethane sulfonic acid (12 ml) is added in several portions sodium nitrite (0.64 g, 0.0093 mol). The solution is heated to 60° C. and stirred overnight. The solution is poured onto a mixture of ethyl acetate and ice. Then, 2N NaOH was added until the aqueous phase was alkaline. The organic phase is washed with water and concentrated in vacuo. The product is purified by flash column chromatography on silica gel (7:3 hexanelethyl acetate) affording the title compound. Mass M+H 400; mp 106–108° C.

Example 9

6-Phenyl-8-(3-nitrophenyl)-1,7-naphthyridine

To a solution of 6-trifluoromethylsulfonyloxy-8-(3-nitrophenyl)-1,7-naphthyridine (300 mg, 0.75 mmol; prepared according to example 8) in tetrahydrofuran (5 ml) is added phenylboronic acid (118 mg, 0.97 mmol, bis (dibenzylideneacetone) palladium (18 mg, 0.03 mmol), triphenylphosphine (16 mg, 0.06 mmol) and aqueous $Na_2CO_3$ (2N, 1.44 ml). The solution is kept at 60° C. for 20 h. The solution is diluted with ethyl acetate, filtered and washed with 1N NaOH and water. The solvent is removed in vacuo to give pure product. Mass M+H 328. mp 172–175° C.

Example 10

6-Vinyl-8-(3-nitrophenyl)-1,7-naphthyridine

To a solution of 6-trifluoromethylsulfonyloxy-8-(3-nitrophenyl)-1,7-naphthyridine (250 mg, 0.62 mmol prepared according to example 13) in tetrahydrofuran (3 ml) is added vinyltributylstannane (218 mg, 0.68 mmol), bis (dibenzylideneacetone)palladium (14 mg, 0.025 mmol), triphenylphosphine (13 mg, 0.049 mmol) and lithium chloride (78 mg, 1.86 mmol). The mixture is kept at 70° C. overnight. The solution is diluted with ethyl acetate, filtered and washed with water. Preparative thin layer chromatography (8:2 dichloromethane/n-hexane) affords the title compound. Mass M+H 278; mp 145–151° C.

Example 11

6-Ethynyl-8-(3-nitrophenyl)-1,7-naphthyridine

A. 6-trimethylsilylethynyl-8-(3-nitrophenyl)-1,7-naphthyridine is prepared as follows:

To a solution of 6-trifluoromethylsulfonyloxy-8-(3-nitrophenyl)-1,7-naphthyridine (200 mg, 0.50 mmol; prepared according to example 13) in dimethylformamide (1 ml) and triethylamine (0.5 ml) is added ethynyltrimethylsilane (0.078 ml, 0.56 mmol), bis(dibensylideneacetone) palladium (5.8 mg, 0.020 mmol), triphenylphosphine (5.3 mg, 0.020 mmol) and copper iodide (3.8 mg, 0.020 mmol). The mixture is kept at 60° C. for 2 h. The solution is diluted with ethyl acetate and washed with water. The product is purified by flash column chromatography on silica gel (20:0.2 toluene/acetone) affording 6-trimethylsilylethynyl-8-(3-nitrophenyl)-1,7-naphthyridine. (Mass M+H 348; mp 160–163° C.)

B. To a solution of 6-trimethylsilylethynyl-8-(3-nitrophenyl)-1,7-naphthyridine (77 mg, 0.22 mmol) in methanol (0.5 ml) and toluene (0.5 ml) is added 1N potassium hydroxide (0.22 ml). The mixture was stirred for 2 h. The suspension is filtered and the product washed with water and ether affording the title compound. Mass M+H 276; mp 215° C. decomposition.

Example 12

6-(4-carboxyphenyl)-8-(3-cyanophenyl)-1,7-naphthyridine

To a solution of 6-trifluoromethylsulfonyloxy-8-(3-cyanophenyl)-1,7-napthyridine (2.15 g, 5.67 mmol) in DMF (21.5 ml) is added 4-carboxy-phenylboronic acid (1.13 g, 6.81 mmol), bis(dibenzylidenacetone) palladium (131 mg, 0.23 mmol), triphenylphosphine (95 mg, 0.36 mmol) and aqueous $K_2CO_3$ (2N, 17 ml). The reaction mixture is stirred at 80° for 2.5 h. The hot solution is filtered through cellit and the crude product is precipitated by carefully adding water (10 ml) and aqueous HCl (2N, 8 ml). The suspension is filtered and the crude product is stirred in hot THF (30 ml). The cold suspension is filtered again to yield the title compound (1.12 g). M+H=352. Melting point >300°. Retention time HPLC=7.58 min (column: LiChroCart 125-4, Supersphere 60 RP-select B, 400; eluent: acetonitrile-water (0.1% TFA)=45:55; 1 ml/min; detection at 254 nm).

Example 13

6-(4-carbamoylphenyl)-8-(3-cyanophenyl)-1,7-naphthyridine

To a suspension of 6-(4-carboxyphenyl)-8-(3-cyanophenyl)-1,7-naphthyridine (100 mg, 0.28 mmol) in toluene (2 ml) is added thionylchloride (0.1 ml, 1.37 mmol). the reaction mixture is kept at reflux for 3 hours. The solvent is evaporated and the residue taken up in THF (2 ml). Aqueous ammonia is added and the solution stirred for two hours at ambient temperature. Ethyl acetate is added, and the organic layer is washed with water to yield pure title compound having a melting point of 237–240° C.

Example 14

6-(4-carboxyphenyl)-8-(4-benzo[c]furazanyl)-1,7-naphthyridine

A. 6-Amino-8-methoxy-1,7-naphthyridine

To a solution of sodium (3.2 g, 0.139 mol) in methanol (1400 ml) was added 2-cyano-3-pyridilacetonitrile (20 g, 0.139 mol) and the reaction mixture was stirred for 17 h at ambient temperature. Then, water (700 ml) was added and on evaporating most of the methanol the title compound crystallized out. Melting point 178–180° C.

B. 6-Trifluoromethylsulfonyloxy-8-methoxy-1,7-naphthyridine

To a solution of 6-amino-8-methoxy-1,7-naphthyridine (19 g, 0.108 mol) in a 1:1 mixture of water and trifluoromethane sulfonic acid (380 ml) is carefully added a solution of sodium nitrite (11.2 g, 0.162 mol) in water (40 ml) at 0° C. After 1 h the cooling bath is removed and the reaction mixture stirred for an other hour at ambient temperature. Then, ethyl acetate (500 ml) is added and the solution is neutralized by adding sodium bicarbonate (4N, 1 l). The water phase is extracted again with ethyl acetate (3×500 ml). The organic solvent is evaporated and the crude product is purified by flash column chromatography on silica gel (20:3 toluene/acetone) affording the title compound. M+308; Melting point 99–101° C.

C. 6-(4-carboxyphenyl)-8-methoxy-1,7-naphthyridine

To a solution of 6-trifluoromethylsulfonyloxy-8-methoxy-1,7-napthyridine (1.5 g, 4.86 mmol) in DMF (40 ml) is added 4-carboxy-phenylboronic acid (0.866 g, 5.34 mmol), bis(dibenzylidenacetone) palladium (112 mg, 0.167 mmol), tri-o-tolylphosphine (96 mg, 0.32 mmol) and aqueous $Na_2CO_3$ (14.6 ml, 2N,). The reaction mixture is stirred at 110° for 3 h. The hot solution is filtred through cellit and the solution evaporated to dryness. The crude product is dissolved in hot water (60 ml) and the water phase washed with ethyl acetate (3×50 ml). The product is precipitated from the water phase by carefully adding aqueous HCl (2N, 6 ml). The suspension is filtered and the crude product is stirred again in hot ethyl acetate (50 ml). The cold suspension is filtered to yield the title compound (1.10 g). M+280; Melting point >300°.

D. 6-(4-carboxyphenyl)-8-bromo-1,7-naphthyridine)

To a solution of 6-(4-carboxyphenyl)-8-methoxy-1,7-naphthyridine (250 mg, 0.892 mmol) in DMF (10 ml) is added $PBr_3$ (0.63 ml, 6.63 mmol). The reaction mixture is heated to 100° C. for 30 min. Then, the suspension is poured into water (50 ml) and the solution washed with ethyl acetate (2×50 ml). The organic solvent is removed and the crude product stirred in ether. The suspension is filtered to yield the title compound (215 mg). Melting point 248–250, decomposition.

E. 4-benzo[c]furazanyl boronic acid

To a solution of 4-benzo[c]furazanyl bromide (4 g, 0.020 mol) in tetrahydrofurane (80 ml) and n-pentane (20 ml) is added triethylborate (3.8 ml, 0.022 mol) and N,N,N,N-tetraethylendiamine (3 ml, 0.02 mol). Then, n-BuLi (8.8 ml, 2.5N in hexane, 0.022 mol) is added dropwise at –100° C. and the solution is stirred for 5 minutes more. The reaction mixture is poured into an aqueous solution of saturated ammonium chloride and the water phase is extracted with ethyl acetate. The organic solvent is removed and the crude product is taken up in dichloromethan/n-hexane (5:6). The suspension is filtered to yield the title compound (1.05 g) which is used without further purification.

F. 6-(4-carboxyphenyl)-8-(4-benzo[c]furazanyl)-1,7-napthyridine

To a solution of 6-(4-carboxyphenyl)-8-bromo-1,7-naphthyridine (100 mg, 0.304 mmol) in DMF (2.5 ml) is added 4-benzo[c]furazanyl boronic acid (60 mg, 0.36 mmol), bis(dibenzylidenacetone) palladium (7 mg, 0.0122 mmol), tri-o-tolylphosphine (7.4 mg, 0.024 mmol) and aqueous Na$_2$CO$_3$ (0.9 ml, 2N). The reaction mixture is stirred at 80° for 2 h. The hot solution is filtred through cellit and the solution evaporated to dryness. The residue is stirred in ethyl acetate (20 ml), the suspension is filtered and the organic solvent is removed. The residue is dissolved in hot DMF (7 ml) and the crude product is precipitated by carefully adding aqueous HCl (2N, 1 ml). The crude product in recrystallized from hot DMF to yield the title compound (68 mg). MH+369; Melting point >300° C. M+H=369. Retention time HPLC=10.40 min (column: LiChroCart 125-4, Supersphere 60 RP-select B, 40°; eluent: acetonitril-water (0.1% TFA)=45:55; 1 ml/min; detection at 254 nm).

By repeating the procedure described in the appropriate example above and using appropriate starting materials the following compounds of formula I are obtained as identified below in Table 1

TABLE 1

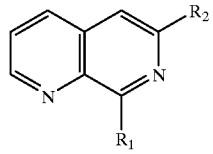

I

| Example No. | R$_1$ | R$_2$ | melting point °C. |
|---|---|---|---|
| 15 | 3-chlorophenyl | —NH$_2$ | 141–143 |
| 16 | 3-cyanophenyl | " | 173–176 |
| 17 | 4-(tetrazol-5-yl)phenyl | " | |
| 18 | —CH$_2$—phenyl | —NH—phenyl | 95–98 |
| 19 | " | N(phenyl)(N-methyl-phenyl) | 60 |
| 20 | " | —O—S(O)$_2$—CF$_3$ | 92–95 |
| 21 | 3-chlorophenyl | " | 94–96 |

TABLE 1-continued
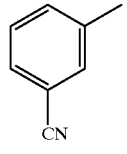
I
| Example No. | R₁ | R₂ | melting point °C. |
|---|---|---|---|
| 22 | 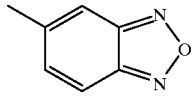 | " | 102–104 |
| 23 | 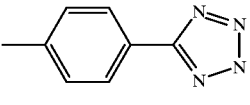 | " | 95–98 |
| 24 | 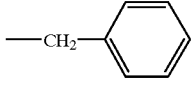 | " | 155–158 |
| 25 | 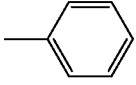 | 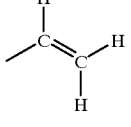 | |
| 26 | " |  | |
| 27 | " | —C≡C—H | |
| 28 | 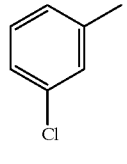 | 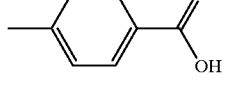 | 265–267 |
| 29 | 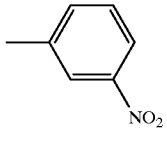 | " | >260 decomp. |
| 30 | 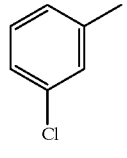 | 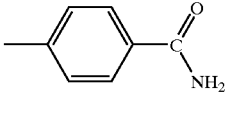 | 234–236 |
| 31 | 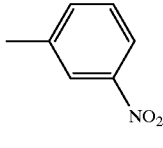 | " | 295 decomp. |

TABLE 1-continued

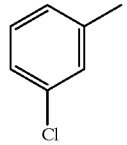

| Example No. | R₁ | R₂ | melting point °C. |
|---|---|---|---|
| 32 | 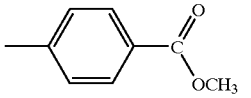 | 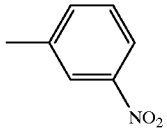 | 225–227 |
| 33 | | " | 214–216 |

Base addition salts of compounds having free carboxy groups, e.g. as described above, may be prepared by contacting the compound with an appropriate amino sugar, e.g. N-methyl-D-glucamine. The following Example is illustrative of the preparation of such base addition salts.

Example 34

6-(4-carboxyphenyl)-8-(4-benzo[c]furazanyl)-1,7-napthyridine: salt with N-methyl-D-glucamine To a hot solution of 6-(4-carboxyphenyl)-8-(4-benzo[c]furazanyl)-1,7-naphthyridine (1 g, 2.72 mmol) in DMF (100 ml) is added N-methyl-D-glucamine (0.53 g, 2.72 mmol). The solvent is removed under reduced pressure and the residue is recrystallized from hot methanol (ca. 50 ml) to yield pure product (1.11 g). Melting point: 230° C., decomposition. Retention time HPLC=6.65 min (column: LiChro-Cart 125-4, Supersphere 60 RP-select B, 50°; eluent: gradient from 0%B/100%A to 70%B/30%A in 15 minutes; A: 2.7 g $KHPO_4$/0.027 g $Na_2HPO_4$ in 900 ml water/100 ml acetonitrile and B: 100 ml water/900 ml acetonitril; detection at 220 nm). The product is water soluble.

8-Aryl-1,7-naphthyridines of the invention, e.g., of formula I, and in particular the preferred 6-(carboxy-, or carboxymethyl- -phenyl)-8-(phenyl, benzo[c]thiadazolyl or benzo[c]furazanyl)-1,7-naphthyridines, and esters and amides thereof, in free or salt form (hereinafter referred to as AGENTS OF THE INVENTION) exhibit pharmacological activity and are useful as pharmaceuticals, e.g. for therapy, in the treatment of diseases and conditions as hereinafter set forth.

In particular AGENTS OF THE INVENTION exhibit cyclic nucleotide phosphodiesterase (PDE) isoenzyme inhibiting activity, selective for type 4 isoenzyme.

AGENTS OF THE INVENTION possess anti-inflammatory, anti-airways hyperreactivity and bronchodilator properties. They further possess immunosuppressive, TNFα secretion inhibitory and other pharmacological activities as may be demonstrated in standard test methods for example as follows:

A. PDE4 inhibition: Recombinant PDE4A, PDE4B, PDE4C and PDE4D isoenzyme inhibition assays.

Cloning and expression: PDE4 cDNA coding for the four isoenzymes, human PDE4A (as described by Sullivan et al., Cell Signal 1994; 6:793–812), rat PDE4B (as described by Colicelli et al., Proc. Natl. Acad. Sci. USA 1989; 86:3599–3903), human PDE4C (as described by Engels et al., FEBS Lett. 1995; 358:305–310), and human PDE4D (as described by Baecker et al., Gene 1994; 138:253–256) is cloned either into an extrachromosomal yeast expression vector (PDE4C, PDE4D) or integrated (PDE4A, PDE4B; single copy) at the pep4 locus of a Saccharomyces cerevisiae strain lacking both of the wild-type yeast PDE genes. Yeast strains expressing PDE4 isoenzymes are grown in 1 l cultures at 30° C., pelleted and frozen until homogenization.

Homogenization: Pelleted yeast (5 mL) is suspended in 50 mL of buffer (10 mM tris-hydroxymethylaminomethane, 1 mM ethylenediamine-tetraacetic acid, 1 mg/mL each of leupeptin and pepstatin A, 175 mg/mL phenylmethylsulphonyl fluoride, 1 mM dithiothreitol, pH 7.4 with HCl). After centrifugation, 15 g of glass beads (425–600 mm, acid washed, Sigma Chemical Co.) washed with buffer are added to the pellet. To this slurry, 1 mL of buffer and 60 mg of cholamidopropane sulphonic acid are added and the slurry is vigorously agitated for 4 h at 4° C. The yeast cells are disintegrated, as observed microscopically (phase-contrast optics) as dark cells and is >30% (usually 50%). The slurry is transferred to a coarse glass funnel and the homogenate collected by suction and washing of the glass beads with a total of 15 mL buffer. Cell fragments are separated from cytosol by centrifugation (2000×g, 10 min, 4° C.). The pellet is resuspended in 15 mL of buffer and assayed for PDE activity together with the cytosol.

Otherwise isoenzyme preparations are derived from human sources. Type 3 and 4 preparations are obtained taking advantage of the predominance of type 3 isoenzymes in platelets and of type 4 isoenzymes in neutrophils applying the following techniques:

Cells and tissues are homogenized on ice in tris-HCl 10 mM pH 7.4 containing: Sucrose (250 mM), EDTA 1 mM, dithiothreitol (1 mM), leupeptin and pepstatin A (1 μg/ml each), and phenyl-methyl-sulphonyl fluoride (PMSF, 0.17 mg/ml added just before the homogenization). Neutrophils (type 4) and platelets (types 2 and 3) are obtained from human blood and sonicated (Branson probe, 4×15 sec.). Human lung (types 1 and 5) is obtained from patients undergoing surgery and homogenized using a Polytron homogenizer (two bursts of 30 sec).

Isoenzyme preparations: PDE 3 and 4 (substrate cAMP 1 $\mu$M) preparations consist of low-speed supernates of the platelet and neutrophil homogenates, respectively. Types 1 (substrate cAMP 1 $\mu$M, $Ca^{2+}$ 0.5 mM, calmodulin 125 nM), 2 (cAMP 100 $\mu$M) and 5 (cGMP 1 $\mu$M) are separated by anion-exchange chromatography (Q-Sepharose) using a gradient of NaCl in homogenization buffer without sucrose and PMSF (0 to 0.1 M NaCl in 2.5 column volumes, 0.1 to 0.45 M in 24 column volumes). PDE 1: fractions where hydrolysis of cAMP 1 $\mu$M can be stimulated by $Ca^{2+}$+calmodulin (0.5 mM and 125 nM, respectively); eluting at 0.17–0.18 M NaCl. PDE 2: fractions showing substantial cAMP hydrolytic activity at 100 $\mu$M but not at 1 $\mu$M; eluting at 0.31–0.32 M NaCl. PDE 5: fractions selectively hydrolysing cGMP 1 $\mu$M over cAMP 1 $\mu$M; eluting at 0.20–0.24 M NaCl.

PDE assay: The assay protocol is based upon the two-step method described by Thompson et al. (Adv. Second Messenger Phosphoprotein Res. 1979; 10:69–92), modified for 96-well microtitre plates. Briefly, enzyme is diluted with homogenization buffer (see above) in order to obtain between 10% and 30% total substrate hydrolysis during the assay. To start the reaction, 25 mL of diluted enzyme is added to 25 mL of substrate ([3H]-cAMP, 1.25 mM, 740 Bq) and 75 mL of inhibitor solution (see below). After 30 minutes at 37° C., the reaction is stopped in a hot water bath (65° C., 5 minutes). Plates are cooled on ice and incubated for 10 minutes at 37° C. with 25 mL of 5'-nucleotidase (Snake venom, from oiophaghus hannah, Sigma Chemical Co., 0.1 mg/mL in water). The unreacted substrate is separated from [3H]-adenosine by sequentially adding aliquots (100+50+50 mL, at 5 min intervals) of 30% (v/v) Dowex 1×2 slurry (acetate form) in 0.2% (v/v) acetic acid. The Dowex is pelleted by centrifugation (150×g, 5 min). Aliquots of the supernates are transferred onto 96-well, solid-phase scintillation plates (LumaPlate, Canberra Packard) using an automated pipetting device (Hamilton MicroLab 2200), dried (at least 4 h at 50° C.) and counted (Canberra Packard TopCount).

Inhibitors: Inhibitor stock solutions are prepared in dimethylsulphoxide (DMSO) and diluted with water/DMSO to achieve 7 concentrations selected to cover the range of 30% to 70% inhibition. The concentration of DMSO is kept constant at 50 mL/mL throughout the assay.

Determination of inhibition parameters: The concentration at which half-maximal inhibition occurs ($IC_{50}$) and the steepness of the dose-response curve (Hill's coefficient) are determined from concentration-inhibition curves by non-linear least-squares fitting to the two-parameter logistic equation. Results are expressed as the negative decimal logarithm of inhibitor concentration at which half-maximal inhibition is observed ($IC_{50}$) (in mol/L; $pIC_{50}$). 95% confidence intervals were estimated and expressed as pL and pU (negative decimal logarithms of the lower and upper confidence limits, respectively). Concentrations which cause a visible precipitation in the assay are excluded from the analysis.

In this test method AGENTS OF THE INVENTION predominantly inhibit PDE isoenzymes of type 4 having relatively little effect in relation to types 1, 2, 3 and 7. Within the PDE type 4 isoenzyme group (i.e. PDE types 4 A to D) AGENTS OF THE INVENTION generally exhibit selectivity for inhibition of PDE type 4 D isoenzyme in comparison with the PDE type 4A, 4B and 4C isoenzymes.

Anti-inflammatory activity: Inhibition of eosinophil activation by formyl-MetLeuPhe (fMLP)

Purified human eosinophils ($10^4$/well in 0.2 ml HBSS) are stimulated with fMLP (1 $\mu$M) in the presence of lucigenin (25 $\mu$M). Inhibition of the oxidative burst (measured as changes in chemiluminescence) is determined from dose response curves using the logistic equation.

AGENTS OF THE INVENTION are active in the above test method at concentrations of the order of from 0.001 to 5 $\mu$M, generally in the low nM range. The compound of example 2 for instance has an $IC_{50}$ in this assay of 0.006 $\mu$M.

Having regard to their anti-inflammatory activity, their influence on airways hyperreactivity and their profile in relation to PDE isoenzyme inhibition, in particular as selective type 4 inhibitors, AGENTS OF THE INVENTION are useful for the treatment, in particular prophylactic treatment, of obstructive or inflammatory airways disease. Thus by continued and regular administration over prolonged periods of time AGENTS OF THE INVENTION are useful in providing advance protection against recurrence of bronchoconstrictor or other symptomatic attack consequential to obstructive or inflammatory airways disease or for the control, amelioration or reversal of basal status of such disease.

Having regard to their bronchodilator activity AGENTS OF THE INVENTION are useful as bronchodilators, e.g. for the treatment of chronic or acute broncho-constriction, e.g. for the symptomatic treatment of obstructive or inflammatory airways disease.

The words "treatment" and "treating" as used throughout the present specification and claims in relation to obstructive or inflammatory airways disease are to be understood accordingly as embracing both prophylactic and symptomatic modes of therapy.

In accordance with the foregoing the present invention further provides

A. A method
  a) for the treatment of airways hyperreactivity,
  b) of effecting bronchodilation or, in particular,
  c) of treating obstructive or inflammatory airways disease, in a subject in need thereof, which method comprises administering to said subject an effective amount of an AGENT OF THE INVENTION.

Obstructive or inflammatory airways diseases to which the present invention applies include asthma, pneumoconiosis, chronic obstructive airways or pulmonary disease (COAD or COPD) and adult respiratory distress syndrome (ARDS), as well as exacerbation of airways hyperreactivity consequent to other drug therapy, e.g. aspirin or β-agonist therapy.

The present invention is applicable to the treatment of asthma of whatever type or genesis, including intrinsic and, especially, extrinsic asthma. It is applicable to the treatment of allergic (atopic/IgE-mediated) asthma. It is also applicable to the treatment of non-atopic asthma, including e.g. bronchitic, exercise induced and occupational asthma, asthma induced following bacterial infection and other non-allergic asthmas. It is further applicable to the treatment of wheezy infant syndrome (infant, incipient asthma).

The invention is applicable to the treatment of pneumoconiosis of whatever type or genesis including, for example, aluminosis, anthracosis, asbestosis, chalicosis, ptilosis, siderosis, silicosis, tobacoosis and byssinosis.

The invention is applicable to the treatment of COPD or COAD including chronic bronchitis, pulmonary emphysaema or dyspnea associated therewith.

The invention is also applicable to the treatment of bronchitis of whatever type or genesis including, e.g. acute, arachidic, catarrhal, chronic, croupus or phthinoid bronchitis etc.

Having regard to their activity as selective inhibitors of TNF-α release, AGENTS OF THE INVENTION are also useful for the down-regulation or inhibition of TNF-α release, e.g. for the treatment of diseases or conditions in which TNF-α release is implicated or plays a mediating role, e.g. diseases or conditions having an aetiology involving or comprising morbid, for example undesirable, excessive or unregulated TNF-α release, in particular for the treatment of cachexia or endotoxin shock and in treatment of AIDS [cf. Sharief et al, Mediators of Inflammation, 1 323–338 (1992)].

The method of the invention is applicable to the treatment of cachexia associated with morbid TNF-α release or TNF-α blood-serum levels of whatever origin, including cachexia consequential to, e.g. bacterial, viral or parasitic, infection or to deprivation or deterioration of humoral or other organic, e.g. renal function. It is for example applicable to the treatment of cancerous, malarial and vermal cachexia, cachexia resulting from dysfunction of the pituitary, thyroid or thymus glands as well as uremic cachexia. It is in particular applicable to the treatment of AIDS-related cachexia, i.e. cachexia consequential to or associated with to HIV infection.

The method of the invention is also applicable to the treatment of septic shock, e.g., shock conditions resulting from bacterial infection. In this regard it is to be noted that the present invention provides a method for the treatment of septic shock as such as well as of conditions consequential to or symptomatic of septic or shock, for example ARDS (adult respiratory distress syndrome).

The method of the invention is further applicable to the treatment of disease consequential to HIV infection, e.g. AIDS, e.g. to the amelioration or control of the advance of such disease.

Having regard to their profile in relation to inhibition of PDE isoenzymes and/or TNFα release inhibition, as well as their immunosuppressive activity, AGENTS OF THE INVENTION are also useful as immunosuppressive agents, e.g. for the treatment of autoimmune diseases, in particular for the treatment of autoimmune diseases in which inflammatory processes are implicated or which have an inflammatory component or aetiology, or as anti-inflammatory agents for the treatment of inflammatory disease in particular for the treatment of inflammatory disease in which autoimmune reactions are implicated or having an autoimmune component or aetiology.

Examples of such disease to which the present invention is applicable include autoimmune hematological disorders (e.g. hemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease) endocrine ophthalmopathy, Grave's disease, sarcoidosis, alveolitis, chronic hypersensitivity pneumonitis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy), as well as inflammatory and/or hyperproliferative skin diseases such as psoriasis atopic dermatitis, pemphigus and, in particular, contact dermatitis, e.g. allergic contact dermatitis.

AGENTS OF THE INVENTION are in particular useful for the treatment of arthritis, and other rheumatic or inflammatory disease, especially for the treatment of rheumatoid arthritis.

As immunosuppressants AGENTS OF THE INVENTION are further indicated for use in the prevention of graft rejection, e.g. for the maintenance of allogenic organ transplants or the like, e.g. in relation to kidney, liver, lung, heart, heart-lung, bowel, bone-marrow, skin, or corneal transplant.

Having regard to their anti-inflammatory activity, in particular in relation to inhibition of eosinophil activation, AGENTS OF THE INVENTION are also useful for the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoal) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Having regard to their profile in relation to inhibition of PDE isoenzymes, in particular their profile as selective type 4 inhibitors, AGENTS OF THE INVENTION are further useful as type 4 PDE inhibitors, for example for the treatment of disease involving tissue calcium depletion, in particular degenerative diseases of the bone and joint involving calcium depletion, especially osteoporosis. In this regard they are further useful for the treatment of allergic inflammatory diseases such as rhinitis, conjunctivitis, atopic dermatitis, urticaria and gastro-intestinal allergies; as vasodilators, e.g. for the treatment of angina, hypertension, congestive heart failure and multi-infarct dementia; and for the treatment of other conditions where inhibition of PDE 4 is indicated, for example, depression, conditions and diseases characterized by impaired cognitive function including Alzheimer's disease, Parkinson's disease and stroke.

Having regard to their ability to interact synergistically with immunosuppressive and/or anti-inflammatory drug substances, AGENTS OF THE INVENTION are also useful as co-therapeutic agents for use in conjunction with such drugs, e.g. as potentiators of therapeutic activity of such drugs or as means of reducing required dosaging or potential side effects of such drugs. Drug substances with which AGENTS OF THE INVENTION may suitably be co-administered include, e.g. cyclopeptide, cyclopeptolide or macrolide immunosuppressive or anti-inflammatory drug substances, for examples drugs belonging to the cyclosporin class, e.g. cyclosporins A or G, the drug substances tacrolimus (also known as FK 506), ascomycin and rapamycin and their various known congeners and derivatives, as well as glucocorticosteroid drugs. Diseases to which such co-therapy may be applied include e.g. any disease or condition requiring immunosuppressive or anti-inflammatory drug therapy, e.g. as hereinbefore set forth.

In particular AGENTS OF THE INVENTION are suitable for use in co-therapy as aforesaid, e.g. for the purposes of immunosuppressive, anti-inflammatory or anti-asthmatic treatment, e.g. to achieve cyclosporin, e.g. cyclosporin A-, macrolide- or steroid-sparing effect.

In accordance with the foregoing the present invention also provides:

B. A method
 a) for the down-regulation or inhibition of TNF-α release,
 b) for the inhibition of PDE 4 isoenzyme activity,
 c) of effecting immunosuppression,
 d) for the treatment of inflammatory disease, or
 e) for the treatment of any particular condition or disease as hereinabove set forth,
in a subject in need thereof, which method comprises administering to said subject an effective amount of an AGENT OF THE INVENTION.

The present invention also provides:

C. An AGENT OF THE INVENTION for use as a pharmaceutical, for example for use in any method or in the treatment of any disease or condition as hereinbefore set forth, e.g. as defined under A or B above.

Dosages employed in practicing the present invention will of course vary depending, e.g. on the particular disease or condition to be treated, the particular AGENT OF THE INVENTION used, the mode of administration and the therapy desired. In general, however, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered 1× or in divided doses 2 to 4× daily or in sustained release form. Unit dosage forms for oral administration thus suitably comprise from about 0.2 to 75 or 150, e.g. from about 0.2 or 2.0 to 50, 75 or 100 mg AGENT OF THE INVENTION, together with a pharmaceutically acceptable diluent or carrier therefor.

For use in the treatment of chronic or obstructive airways disease, e.g. asthma AGENTS OF THE INVENTION may also be administered by the inhaled route. Again dosages employed will vary, e.g. depending on the particular disease or condition, the particular AGENT OF THE INVENTION employed, the particular mode of administration (e.g. whether by dry powder inhalation or otherwise) and the effect desired. In general, however, an indicated inhaled daily dosage will be of the order of from about 2.5 to about 130.0 μg/kg/day e.g. from about 13.0 to about 60.0 μg/kg/day. For larger mammals, for example humans, an indicated daily dosage for administration by inhalation, e.g. in the treatment of asthma, will be in the range of from about 0.2 to about 10.0 mg, e.g. from about 1 to about 5 mg, conveniently given in one single administration or 2 or 3 separate administrations throughout the day. An appropriate dosage per administration will thus be of the order of from about 200 μg to about 3.3 mg, with administration up to 3 times daily, suitably administered from a dry powder inhalation delivery device in a series of 2 to 8 puffs at each administration.

AGENTS OF THE INVENTION may also be administered by any other appropriate route, e.g. by infusion, for example for the treatment of endotoxin shock; nasally, for example for the treatment of rhinitis; ocularly, for example for the treatment of autoimmune diseases of the eye; dermally, i.e. topically to the skin, for example for the treatment of dermatoses or psoriasis; or rectally, e.g. via enemation or suppository, for example for the treatment of inflammatory bowel disease. Suitable dosages for application by such routes will generally be of the order of 10 to 100× less than those required for oral administration.

Pharmaceutical compositions comprising AGENTS OF THE INVENTION may be prepared using conventional diluents or excipients and techniques known in the galenic art. Thus oral dosage forms may include tablets, capsules and the like. Formulations for dermal administration may take the form of creams, ointments, gels, or transdermal delivery systems, e.g. patches and, in addition to inert diluents or carriers, may suitably contain skin penetration enhancing agents, again as known in the art.

Compositions for inhalation may comprise aerosol or other atomizable formulations as well as inhalable dry powder formulations, with or without diluent, for administration by any appropriate dry powder inhalation system as known in the art. For the preparation of dry powder forms for inhalation, AGENTS OF THE INVENTION are suitably employed in pharmaceutically acceptable acid addition salt form. The said salt form is suitably milled, e.g. using an air-jet or ceramic mill to provide a finely divided inhalable powder, e.g. having an average particle diameter of ca. 2–3μ. Appropriately at least 90% of the material will have an average particle diameter of less than 7.8μ, more preferably of less than 4.8μ. In order to ensure obtention of an appropriate and consistent particulate product suitable for administration by inhalation in dry powder from, it may be preferable to effect milling of the active ingredient premixed with an appropriate inhalable carrier medium, e.g. lactose, under conditions of reduced temperature.

In accordance with the foregoing the present invention also provides: a pharmaceutical composition comprising an agent of the invention together with a pharmaceutically acceptable diluent or carrier therefor, e.g. for use in any method as hereinbefore defined.

What is claimed is:

1. An 8-aryl-1,7-naphthyridine or N-oxide thereof, substituted in the 6-position by hydroxy, allyl, alkyl, alkenyl, alkynyl, alkoxy, carboxyphenyl, carboxymethylphenyl, aryloxy, amino, trifluoromethanesulfonyloxy, arylamino, diarylamino, alkamino, dialkamino, arylamido or an alkamido where the 8-aryl group is a mono- or bicyclic aromatic or heteroaromatic moiety having up to 10 aromatic non-hydrogen atoms and is linked to the 1,7-naphthyridine either directly or via a methylene bridge, or an ester or amide thereof, in free or salt form.

2. A compound according to claim 1 of formula I

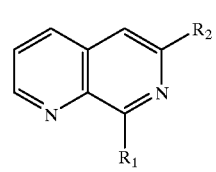

wherein
 $R_1$ is phenyl, benzyl, 3-nitrophenyl, 3-chlorophenyl, 3-cyanophenyl, 3-(tetrazolyl) phenyl, benzofurazanyl, or benzothiadiazolyl;
 $R_2$ is hydroxy, amino, trifluoromethanesulfonyloxy, allyl, alkyl, alkenyl, alkynyl, alkoxy, aryl, aralkyl, aryloxy, amino, arylamino, diarylamino, alkamino, dialkamino, alkaryl, arylamido, or alkamido, or an ester or amide thereof;
in free or salt form.

3. A compound according to claim 1 which is a 6-(carboxyphenyl or carboxymethylphenyl)-8-(phenyl, benzo[c]thiadiazolyl or benzo[c]furazanyl)-1,7-naphthyridine, or an ester or amide thereof, in free or pharmaceutically acceptable salt form.

4. A compound according to claim 3 of formula II

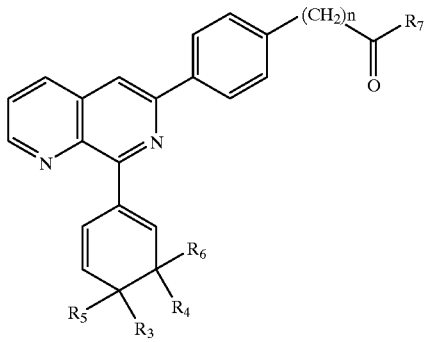

wherein
  n is zero or one;
  $R_7$ is hydroxy, amino, $C_{1-4}$alkylamino, or $C_{1-4}$alkoxy, and either
  $R_3$ is H and $R_4$ is nitro, halo, cyano, or tetrazolyl and $R_5$ and $R_6$ together form an additional bond, or $R_3$, $R_4$, $R_5$ and $R_6$ together are =N—O—N= or =N—S—N=;
in free or pharmaceutically acceptable salt form.

5. A compound according to claim 4, wherein $R_7$ is hydroxy or amino.

6. A compound according to claim 4, wherein halo is chloro.

7. A compound according to claim 4, wherein tetrazolyl is 5-tetrazolyl.

8. A compound according to claim 2 which is
6-amino-8-(3-nitrophenyl)-1,7-naphthyridine,
6-amino-8-(4-benzo[c]furazanyl)-1,7-naphthyridine,
6-hydroxy-8-(3-nitrophenyl)-1,7-naphthyridine,
6-methoxycarbonylmethoxy-8-(3-nitrophenyl)-1,7-naphthyridine,
6-acetamido-8-(3-nitrophenyl)-1,7-naphthyridine hydrochloride,
6-amino-8-benzyl-1,7-naphthyridine,
6-phenylamino-8-(3-nitrophenyl)-1,7-naphthyridine,
6-trifluoromethanesulfonyloxy-8-(3-nitrophenyl)-1,7-naphthyridine,
6-phenyl-8-(3-nitrophenyl)-1,7-naphthyridine,
6-vinyl-8-(3-nitrophenyl)-1,7-naphthyridine,
6-ethynyl-8-(3-nitrophenyl)-1,7-naphthyridine,
6-(4-carboxyphenyl)-8-(3-cyanophenyl)-1,7-naphthyridine,
6-(4-carbamoylphenyl)-8-(3-cyanophenyl)-1,7-naphthyridine,
6-(4-carboxyphenyl)-8-(4-benzo[c]furazanyl)-1,7-naphthyridine,
6-(4-carboxyphenyl)-8-(4-benzo[c]furazanyl)-1,7-naphthyridine N-methyl-D-glucamine salt,
or a compound of formula I in which
  $R_1$ is 3-chlorophenyl and $R_2$ is amino,
  $R_1$ is 3-cyanophenyl and $R_2$ is amino,
  $R_1$ is 4-(5-tetrazolyl) phenyl and $R_2$ is amino,
  $R_1$ is benzyl and $R_2$ is phenylamino,
  $R_1$ is benzyl and $R_2$ is diphenylamino,
  $R_1$ is benzyl and $R_2$ is trifluoromethanesulfonyloxy,
  $R_1$ is 3-chlorophenyl and $R_2$ is trifluoromethanesulfonyloxy,
  $R_1$ is 3-cyanophenyl and $R_2$ is trifluoromethanesulfonyloxy,
  $R_1$ is 4-benzo[c]furazanyl and $R_2$ is trifluoromethanesulfonyloxy,
  $R_1$ is 4-(5-tetrazolyl)phenyl and $R_2$ is trifluoromethanesulfonyloxy,
  $R_1$ is benzyl and $R_2$ is phenyl,
  $R_1$ is benzyl and $R_2$ is vinyl,
  $R_1$ is benzyl and $R_2$ is ethynyl,
  $R_1$ is 3-chlorophenyl and $R_2$ is 4-carboxyphenyl,
  $R_1$ is 3-nitrophenyl and $R_2$ is 4-carboxyphenyl,
  $R_1$ is 3-chlorophenyl and $R_2$ is 4-aminocarbonylphenyl,
  $R_1$ is 3-nitrophenyl and $R_2$ is 4-aminocarbonylphenyl,
  $R_1$ is 3-chlorophenyl and $R_2$ is 4-methoxycarbonylphenyl, or
  $R_1$ is 3-nitrohenyl and $R_2$ is 4-methoxycarbonylphenyl in free or pharmaceutically acceptable salt form.

9. A process for the preparation of a compound of formula II as defined in claim 4, comprising reacting a compound of formula VI

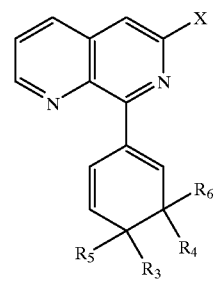

wherein $R_3$, $R_4$, $R_5$, $R_6$ are as defined in claim 4 and X is a leaving group, with a compound of formula VII

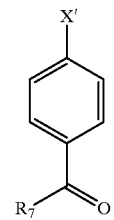

wherein $R_7$ is as defined in claim 4 and X' is a leaving group, and recovering the compound of formula II thus obtained in free or salt form.

10. A compound of formula V'

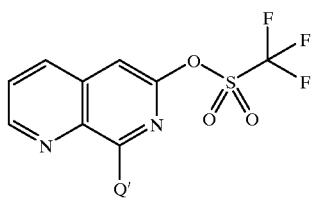

wherein Q' is halogen, or —O—Alk where Alk denotes a $C_1$–$C_8$ alkyl group.

11. A compound of formula VI

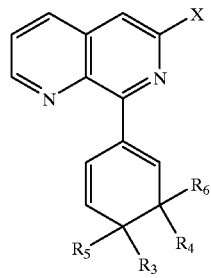

VI wherein $R_3$, $R_4$, $R_5$, $R_6$ are as defined in claim 4 and X is a leaving group.

12. A pharmaceutical composition comprising a compound according to claim 1 together with a pharmaceutically acceptable diluent or carrier therefor.

13. A pharmaceutical composition comprising a compound according to claim 4 together with a pharmaceutically acceptable diluent or carrier therefor.

14. A pharmaceutical composition comprising a compound according to claim 8 together with a pharmaceutically acceptable diluent or carrier therefor.

15. A method for treatment of inflammatory disease in a subject in need thereof, which method comprises administering to said subject an effective amount of a compound according to claim 1.

16. A method for treatment of an obstructive or inflammatory airways disease in a subject in need thereof, which method comprises administering to said subject an effective amount of a compound according to claim 1.

17. A method for treatment of an obstructive or inflammatory airways disease in a subject in need thereof, which method comprises administering to said subject an effective amount of a compound according to claim 4.

18. A method for the down-regulation or inhibition of TNF-α release in a subject in need thereof, which method comprises administering to said subject an effective amount of a compound according to claim 1.

19. A method for the inhibition of PDE 4 isoenzyme activity in a subject in need thereof, which method comprises administering to said subject an effective amount of a compound according to claim 1.

20. A method of effecting immunosuppression in a subject in need thereof, which method comprises administering to said subject an effective amount of a compound according to claim 1.

* * * * *

UNITED STATES PATENT AND TRADEMARK OFFICE
CERTIFICATE OF CORRECTION

PATENT NO. : 6,136,821  
DATED : October 24, 2000  
INVENTOR(S) : Rene Hersperger Page 1 of 1

It is certified that error appears in the above-identified patent and that said Letters Patent is hereby corrected as shown below:

<u>Claim 2,</u>  
Line 1, should read as follows:

-- A compound of formula 1 --.

Signed and Sealed this

Twenty-sixth Day of March, 2002

Attest:

*Attesting Officer*

JAMES E. ROGAN  
*Director of the United States Patent and Trademark Office*